United States Patent [19]

Norén

[11] Patent Number: 5,676,690

[45] Date of Patent: Oct. 14, 1997

[54] APPARATUS FOR ADMINISTERING MEDICAL THERAPY USING DETRENDED FLUCTUATION ANALYSIS OF PHYSIOLOGICAL ACTIVITY

[75] Inventor: Kjell Norén, Solna, Sweden

[73] Assignee: Pacesetter AB, Solna, Sweden

[21] Appl. No.: 761,755

[22] Filed: Dec. 5, 1996

[51] Int. Cl.$^6$ .................................................. A61N 1/365
[52] U.S. Cl. ............................................................ 607/9
[58] Field of Search .............................. 607/2, 4, 5, 9, 607/17

[56] References Cited

U.S. PATENT DOCUMENTS

| | | | |
|---|---|---|---|
| 5,107,850 | 4/1992 | Olive | 607/4 |
| 5,312,443 | 5/1994 | Adams et al. | 607/5 |
| 5,312,452 | 5/1994 | Salo | 607/17 |
| 5,342,401 | 8/1994 | Spano et al. | 607/5 |
| 5,456,690 | 10/1995 | Duong-van | 607/5 |

Primary Examiner—William E. Kamm
Attorney, Agent, or Firm—Hill, Steadman & Simpson

[57] ABSTRACT

An implantable medical apparatus includes a therapy unit which produces a medical therapy regimen which is administered by the implantable medical apparatus to a subject. The implantable medical apparatus obtains an electrical signal representing physiological activity of the subject and performs detrended fluctuation analysis on the electrical signal so as to obtain a self-similarity parameter for the electrical signal. Deviations of the self-similarity parameter from a nominal value indicate the severity of the pathology of the subject which the implanted medical apparatus is intended to treat. The self-similarity parameter can be made extracorporeally available for use by a physician to evaluate the effectiveness of a treatment program currently in place, and/or can be supplied to a control unit of the implantable medical apparatus for use in automatically adjusting the therapy regimen administered by the implantable medical apparatus.

24 Claims, 6 Drawing Sheets

*FIG. 1*  SAMPLED HEART RATE. AVERAGE HEART RATE= 90.57 BPM
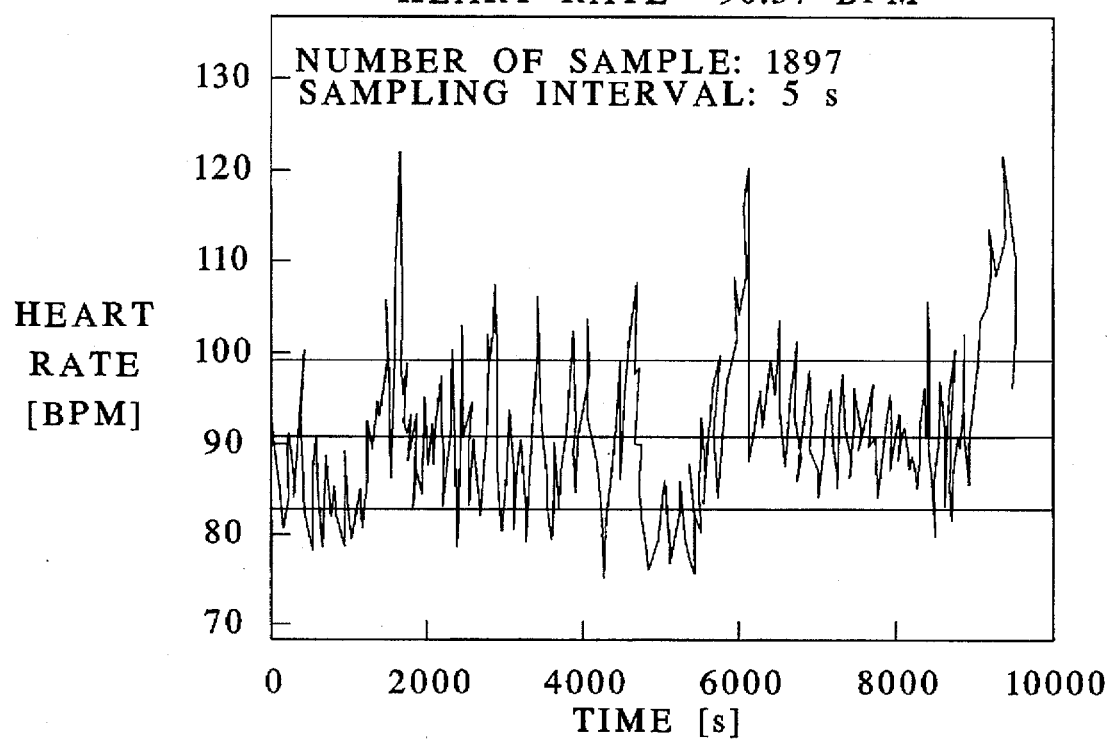
*FIG. 2*
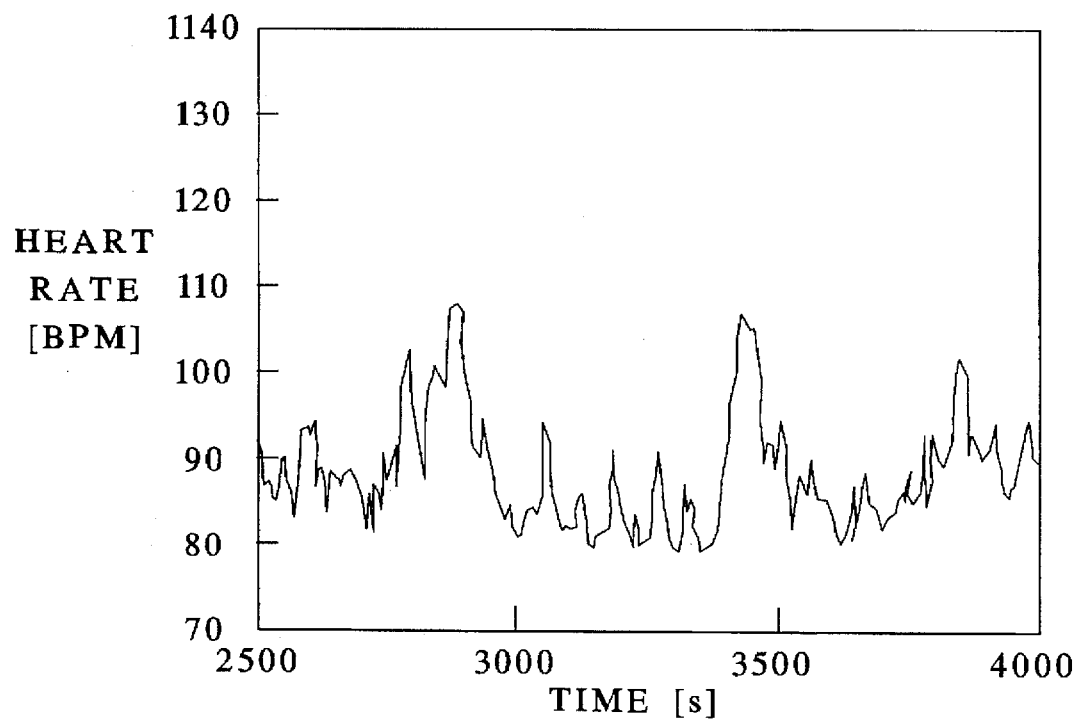

FIG. 3
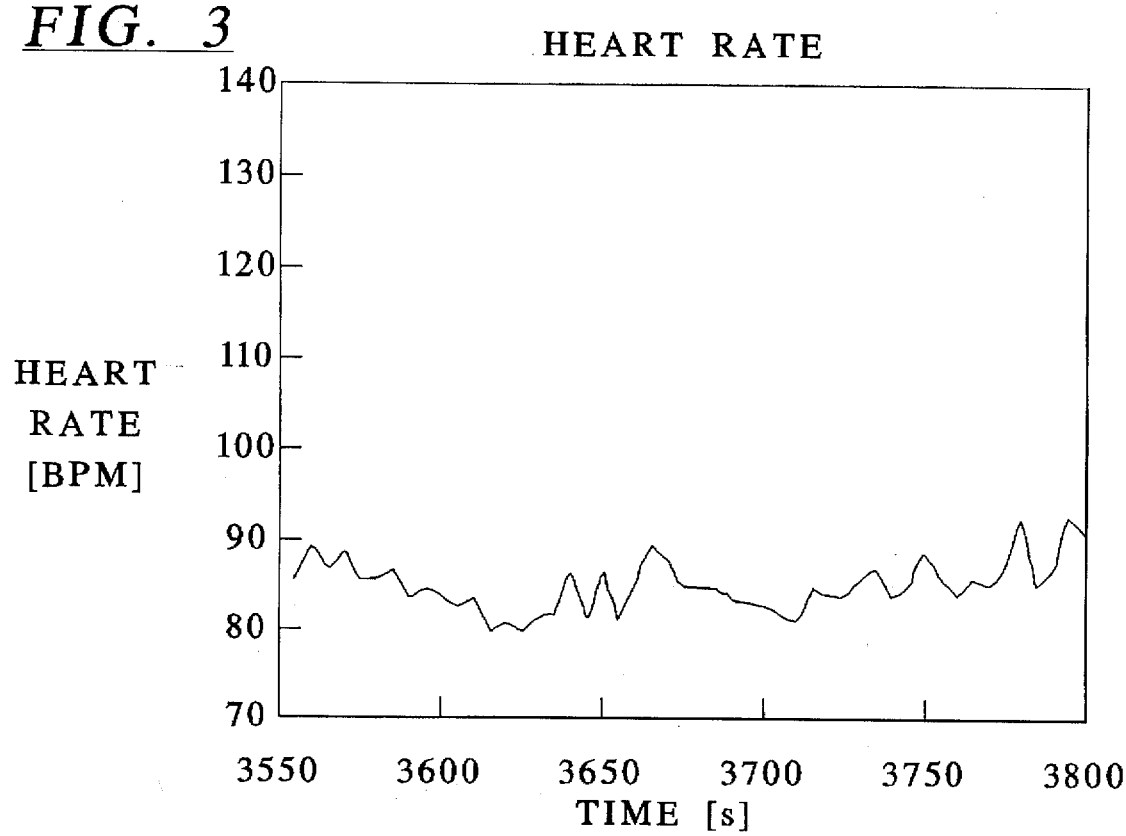
FIG. 4 INTERBEAT INTERVAL TIME SERIES.
AVERAGE RR-int= 0.6677s
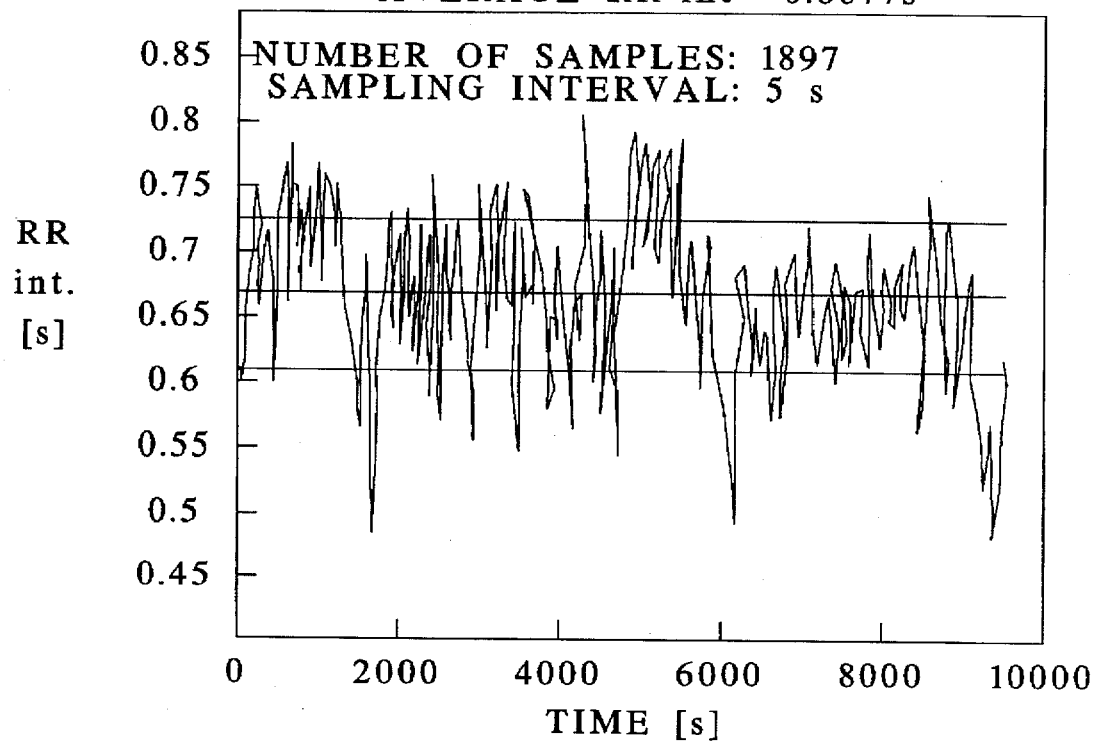

APPARATUS FOR ADMINISTERING MEDICAL THERAPY USING DETRENDED FLUCTUATION ANALYSIS OF PHYSIOLOGICAL ACTIVITY

BACKGROUND OF THE INVENTION

1. Field of the Invention

The present invention is directed to an implantable apparatus for administering medical therapy to a subject of the type wherein the therapy is administered dependent on a measured physiological parameter.

2. Description of the Prior Art

Various implantable medical devices are known wherein the therapy administered by the device is controlled, at least in part, by a measured physiological parameter which represents physiological activity that varies over time. Such devices include, for example, pacemakers, defibrillators, infusion pumps, etc. A common problem in all implantable devices of this type is to administer the therapy in a manner which mimics or simulates as closely as possible the natural activity of the subject which, due to disease or other factors, must be replaced in whole or in part by the implanted device.

When such an implanted device is controlled by a measured physiological activity, further problems arise in the selection of the physiological activity to be monitored, as well as in the analysis of the measured physiological activity in order to interpret the body's needs therefrom and to continually adjust the administered therapy to match these needs as closely as possible.

The type of physiological parameter which is measured is, of course, related to the type of therapy which is to be administered. In the case of an implanted infusion pump, for example, blood sugar level is monitored. In the case of cardiac-assist devices, such as pacemakers, cardioverters and defibrillators, a large number of different physiological parameters have been proposed, as well as different combinations of parameters, for controlling pacing, identifying the presence of arrhythmia, identifying the presence of impending or existing fibrillation, etc. Examples of physiological parameters measured for these purposes include venous blood pressure, blood pressure in the ventricle, filling rate in the ventricle, minute volume, blood oxygen content, respiration, cardiac impedance, atrial cardiac activity, ventricular cardiac activity, etc.

In general, one or more of these physiological parameters is measured in a suitable way, and an electrical signal is produced corresponding to the measured activity. This electrical signal is then subjected to analysis in order to make an evaluation of the body's current needs, as represented by the measured signal. Such analysis can include one or more of identification of maxima and/or minima in the signal, comparison of the maxima and/or minima to respective threshold levels, analysis of the morphology (shape) of the signal waveform, measuring and analyzing any periodicity in the signal, measuring the average value of the signal, etc. To assist in any of these measurements, frequently the signal is either differentiated one or more times, or is integrated, or combinations of differentiation and integration are used.

Each of the above conventional types of signal evaluation has in common that one or more identifiable features of the signal is (are) selected and extracted and is (are) used to control the therapy administration. This requires development of an appropriate data base over relatively long periods of time so that, for a particular patient, the patient's individualized needs as reflected in the measured parameter can be identified, and the therapy can then be matched to those needs. The data base, at the time of implantation, may initially be based on a large patient population, and after the device has been implanted, a data base for that particular patient can be developed over time. While this general approach has been satisfactory for many purposes, a problem still exists in accurately adapting the signal analysis to the needs of a patient which may change over time, or which may change in a daily cycle. For example, if a particular therapy is administered, or is adjusted upwardly or downwardly, dependent on whether a signal peak exceeds a threshold, it is possible, and even likely that due to aging of the patient, lowered patient requirements during nocturnal hours, aging of the implanted device, etc. that the threshold itself may require relatively frequent adjustment. Therefore, not only must the physiological signal be continually evaluated, but also the reliability of the evaluation procedure must be continually monitored and adjusted as needed. Usually, the evaluation procedure is itself evaluated based on the signal characteristic it is designed to monitor. In the case of a signal peak as the signal characteristic, for example, the presence (or absence) of an identified peak for a given number of cardiac cycles over a specified time duration may be used as an indication that adjustment of the threshold is needed.

A signal analysis approach based on chaos theory is finding increasing use in many fields. In general, chaos theory is based on the recognition that a seemingly random signal (i.e., a signal having no apparent periodicity) does, in fact, exhibit characteristics from which a trend can be ascertained, if monitored over long enough periods of time. In the clinical analysis of heart rate dynamics, for example, it has been proposed to analyze a signal representative of cardiac-related activity using a type of analysis known as detrended fluctuation analysis (DFA). The use of this type of analysis based on clinical patient examinations, for the purpose of assessing cardiac risk and forecasting sudden cardiac death, is described in the article "Fractal Mechanisms and Heart Rate Dynamics," Peng et al., Proceedings of the 20$^{th}$ Annual ISCE Conference, Apr. 29–May 4, 1995, reported in Journal of Electrocardiology, Vol. 28 Supplement, pp. 59–64. As described in more detail below, this type of analysis makes use of the concept of self-similarity. This concept is based on the recognition that the same signal, if compared with itself over different time periods, will yield an index (i.e., a dimensionless number) which is indicative of a hidden trend in the signal. As reported in the aforementioned article, after evaluating a suitable number of patients under clinical conditions, a particular index value, such as 1.0, can be assigned to patients having healthy cardiac activity. The extent to which the measured signal of a particular patient produces an index which deviates from this nominal value is an indication of the extent to which that patient is at risk of developing, or is already experiencing, cardiac pathology, such as ischemia.

SUMMARY OF THE INVENTION

An object of the present invention is to provide an implantable apparatus for administering medical therapy which makes an indicator extracorporeally available to a physician which identified the cardiac risk of the patient, and/or which indicates the effectiveness of the therapy currently being administered to the patient either by the implantable apparatus or by other means.

Another object of the present invention is to provide an implantable apparatus for administering medical therapy wherein the administered therapy is delivered based on an evaluation of a characteristic of a measured physiological signal wherein the evaluation procedure can itself be evaluated, and adjusted if necessary, independently of the signal characteristic.

The above object is achieved in accordance with the principles of the present invention in an implantable apparatus for administering medical therapy wherein the administration of the therapy is controlled, at least in part, by undertaking a detrended fluctuation analysis of a measured physiological signal is undertaken and the result of this analysis is made extracorporeally available to a physician and/or is employed internally in the implantable apparatus to automatically evaluate, and to adjust if necessary, an evaluation procedure for the measured physiological signal, or for a different physiological signal, also measured.

The advantage of using detrended fluctuation analysis, heretofore used only for the purpose of conducting clinical evaluation of patients, in an implanted device is that the entire signal is continually analyzed and compared with itself to yield an index. There is thus no need to select which signal characteristics will be evaluated, because the overall signal is continually employed for the analysis. Moreover, there is no need to select evaluation criteria, such as threshold levels, because the signal is being compared with itself. The index obtained as a result of the detrended fluctuation analysis can, however, be used in combination with known, conventional types of sensor signal analysis so as to improve the reliability of such conventional techniques by refining the adjustability thereof to the forecasted long-term needs of the patient.

In implanted devices such as pacemakers and defibrillators, which commonly have telemetry capability so that data can be accumulated over time and then read out via an external programmer, the detrended fluctuation analysis index can be made available to a physician by display on the programmer for use by the physician in making decisions relating to the viability of the therapy currently being administered. The physician can then make determinations as to whether the cardiac risk of the patient, as represented by the index, warrants changes in the therapy, or indicates that an additional therapy, to complement the existing therapy, is advisable. For example, if the index for a patient in whom a pacemaker is implanted indicates that the patient is becoming seriously at risk of experiencing fibrillation, the physician may decide that implantation of a cardioverter or defibrillator is advisable, or perhaps the patient should be placed on a pharmacological regimen in an effort to bring the patient's index back closer to the nominal value. If a pharmacological regimen is prescribed, periodic monitoring of the index can then be used as an indicator of the effectiveness of the regimen.

Employing detrended fluctuation analysis in an implantable device, as opposed to its known use for clinical analysis, has the further advantage of providing a data base obtained over long periods of time during a patient's natural activity. Patient measurements which are made merely during office visits have the disadvantage of being of insufficient time duration to permit long-term effects to be forecasted. Even if measurements are made over a longer period of time, such as by using a Holter monitor, it has frequently been found that measurements obtained under such conditions are sometimes altered, as compared to a patient's natural activity, simply by wearing such a Holter monitor, because the patient refrains from activity in which the patient would normally engage because he or she is aware of being monitored, or because the monitor itself may hinder a particular type of activity.

An embodiment of the invention is disclosed in the form of an implantable pacemaker wherein a sampled RR interval is used as the signal subjected to the detrended functional analysis. The invention has applicability, however, to any type of implanted device for administering medical therapy, and can be used to analyze any type of measured physiological activity.

DESCRIPTION OF THE DRAWINGS

FIG. 1 shows a sampled heart rate over a time of approximately 10,000 seconds, for explaining the concept of self-similarity used in the invention.

FIG. 2 shows the sampled signal of FIG. 1 over an excerpted time duration of 1,500 seconds, for explaining the concept of self-similarity used in the invention.

FIG. 3 shows the sampled heart rate of FIG. 2, over an excerpted time duration of 250 seconds, for explaining the concept of self-similarity used in the invention.

FIG. 4 shows a sampled RR interval signal over a time duration of approximately 10,000 seconds as an example for applying the invention.

DESCRIPTION OF THE PREFERRED EMBODIMENTS

Figure 5:
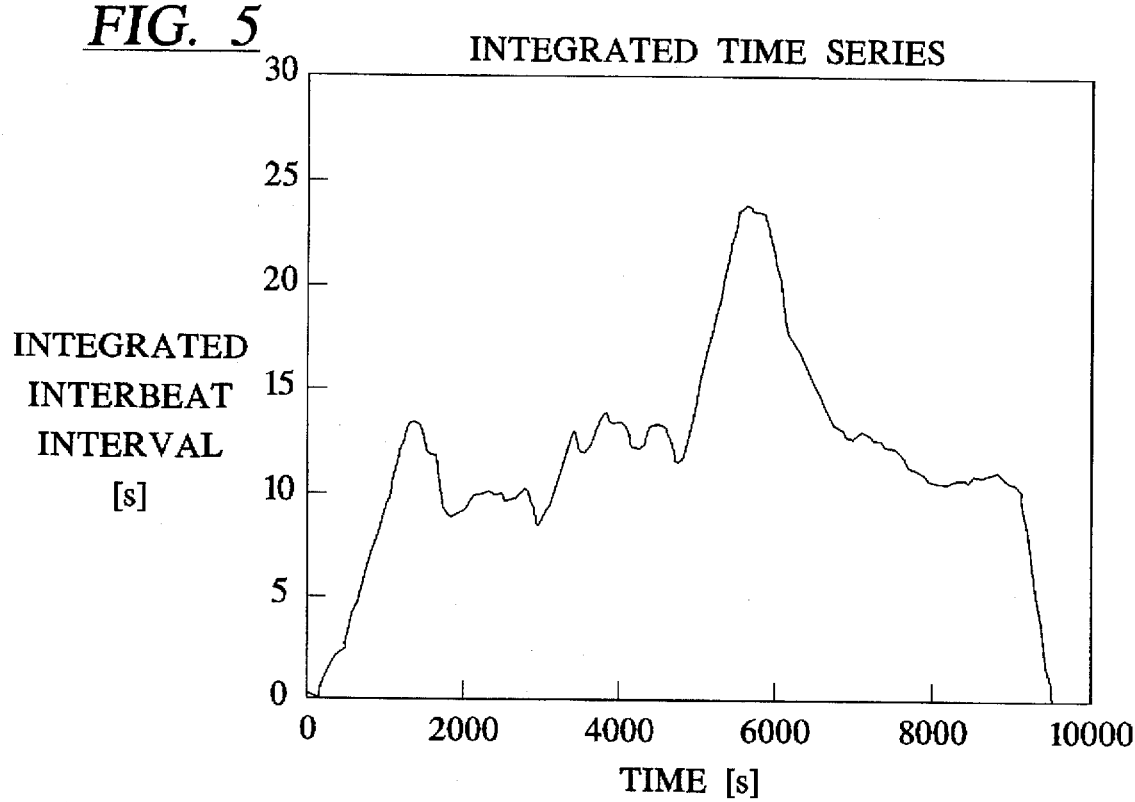
FIG. 5 shows the integrated interbeat interval for the signal of FIG. 4.

Physiological sensor signals measured in a living subject exhibit non-stationary (dynamic) drifts. Although these drifts may cause the signal to appear to be without a pattern, the variation in the measured parameter values is, in most cases, not truly random. Hidden patterns can be found, and are used in accordance with the principles of the present invention to separate signals representing a healthy patient from signals representing a patient experiencing, or who can be expected to experience, cardiac pathology.

Normally, in the context of any type of situation wherein measured signals are obtained, the presence of parameter fluctuations is viewed as a problem, since such fluctuations normally pose analytical difficulties. In the present invention, however, such parameter fluctuations are used to advantage to identify the status of the heart of the subject.

In general, the invention is based on the recognition that the variability of a measured signal parameter can be calculated and compared over different lengths of time. The result of this comparison produces a classification index. A nominal classification index can be identified as representing a healthy heart, and in deviations from this nominal index are then indicative of the presence, or risk, of cardiac pathology.

If a signal representative of normal sinus rhythm is obtained, and the variance of the heart rate is calculated over increasingly longer time windows, the value of the variance increases as the duration of the time window increases. A different situation exists when analyzing a truly random (white noise) situation. In a truly random signal, the variance decreases as the sample size is increased. This is because the variance of a truly random signal is proportional to $1/\sqrt{N}$, where N is the sample size. In a truly random signal, all of the samples are independent of each other. This is not the case for normal sinus rhythm, which is a representative of a type of signal referred to as a 1/f signal, or 1/f noise. For a 1/f signal, the logarithmic slope relative to the sample size is 1.0. The logarithmic slope relative to the sample size is 0.5 for the random (white noise) situation, and is 1.5 for the integrated random case.

In the field of chaos theory, the concept of self-similarity is used as an index or measure of the consistency of fluctuations over time in a given signal. An object or signal is said to be self-similar if a subset thereof can be rescaled to statistically resemble the original object or signal. For example, if a continuous signal measured over a first window (defined by a time duration or a number of samples) is compared with a subset of itself taken from a second, smaller window within the first window, the signal will be said to be self-similar if the result of the comparison of the signal with its subset yields a scaling exponent (slope) of 1.0. This scaling component is called the self-similarity parameter. A self-similarity parameter of 1.0 means that the subset of the signal is experiencing the same dynamic fluctuations as the overall signal; therefore the fluctuations are not truly random, but are identically present in every part of the signal as well as the overall signal itself.

The self-similarity concept applied to a cardiac signal is illustrated in the example shown in FIGS. 1, 2 and 3. FIG. 1 is an example of a recorded heart rate, obtained over two hours and forty minutes (9,600 seconds). The sampling interval was 5 s. FIG. 2 is an excerpt of the curve shown in FIG. 1, but within a smaller window between the time beginning at 2,500 s and ending at 4,000 s, thereby permitting the curve to be illustrated in an expanded form.

FIG. 3 shows an excerpt from the curve of FIG. 2 within an even smaller window, from the time beginning at 3,550 s through 3,800 s. Just by a visual comparison of FIGS. 1, 2 and 3, a general consistency in the overall curve morphology appears to be present. The discussion which follows below explains in detail the manner by which an index can be calculated which represents the degree of similarity among a signal and excerpts thereof. Consistent with the above discussion, the detrended fluctuation analysis used in the present invention is based on the calculated index having a value of 0.5 for white noise (i.e., a completely random process), 1.0 for a healthy sinus rhythm, 1.5 for integrated white noise, and, as an exemplary cardiac pathology, 1.3 for ischemia.

The more detailed analysis below is based on the time between two beats (the 5 s average of the RR-interval). The beat number could have been used as the value represented on the horizontal axis if the beat-to-beat interval have been measured. The discussion which follows tracks the description of detrended fluctuation analysis in the aforementioned Peng et al. article.

First an interbeat interval sample set is obtained, as shown in FIG. 4. Again, these samples were obtained over a time period of two hours and forty seconds with a sampling interval with 5 s, resulting in a number of samples N=1897.

Next, the average level is removed from the data set and the resulting curve is then integrated, thereby resulting in a cumulative sum of the samples, as shown in FIG. 5.

Figure 6:
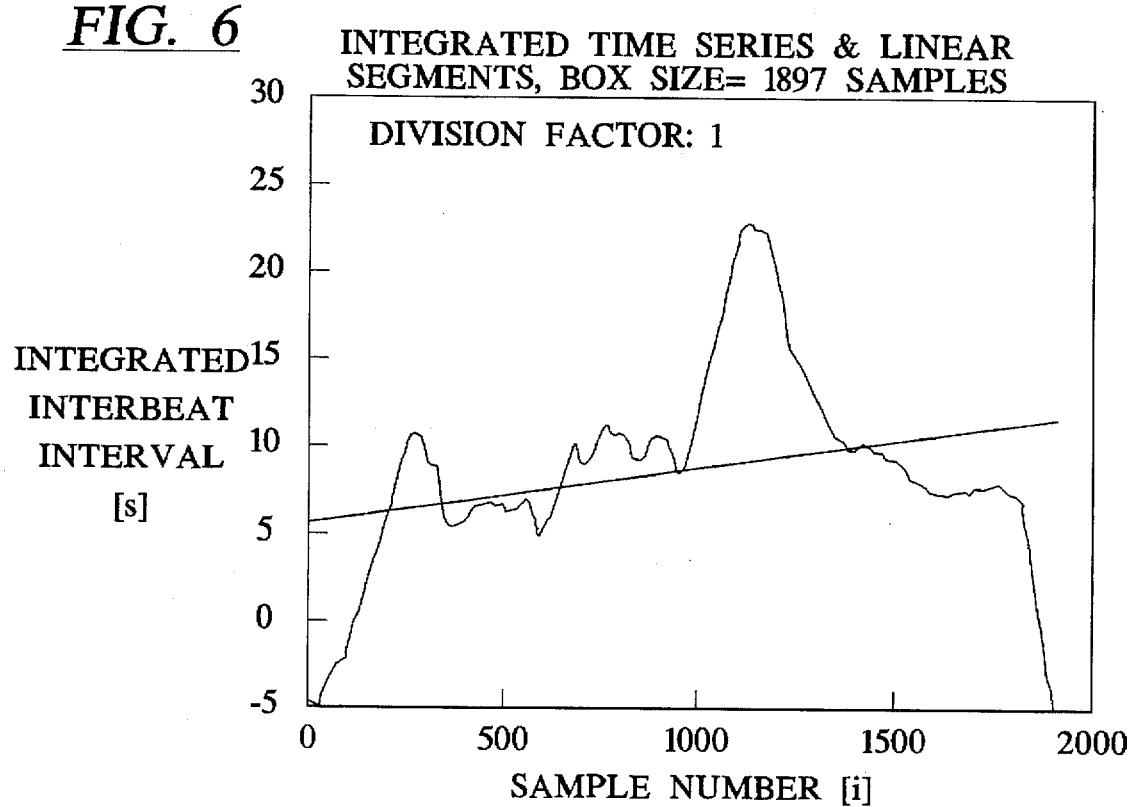
FIG. 6 shows a straight line fit with a division factor of 1 for the integrated interbeat interval curve of FIG. 5.

The next step is to calculate the linear trend in the data, which is accomplished by fitting a straight line (using any suitable "best fit" technique) to the entire measured interval, as shown in FIG. 6. The notation "division factor: 1" indicates that the straight line fit is being undertaken for the entire measured interval, i.e., for a "box size" encompassing all 1,897 samples.

Next, the fluctuations of the integrated signal around this straight line are calculated, using the formula $$F = \sqrt{\frac{1}{N} * \sum_{1}^{N} (YINT - YLIN)^2}$$

wherein N is the number of samples, YINT is the integrated interbeat interval and YLIN is the linear trend. For the above example, F=4.593. Since this value was obtained using a division factor of 1, the value can be designated as F1=4.593.

Figure 7:
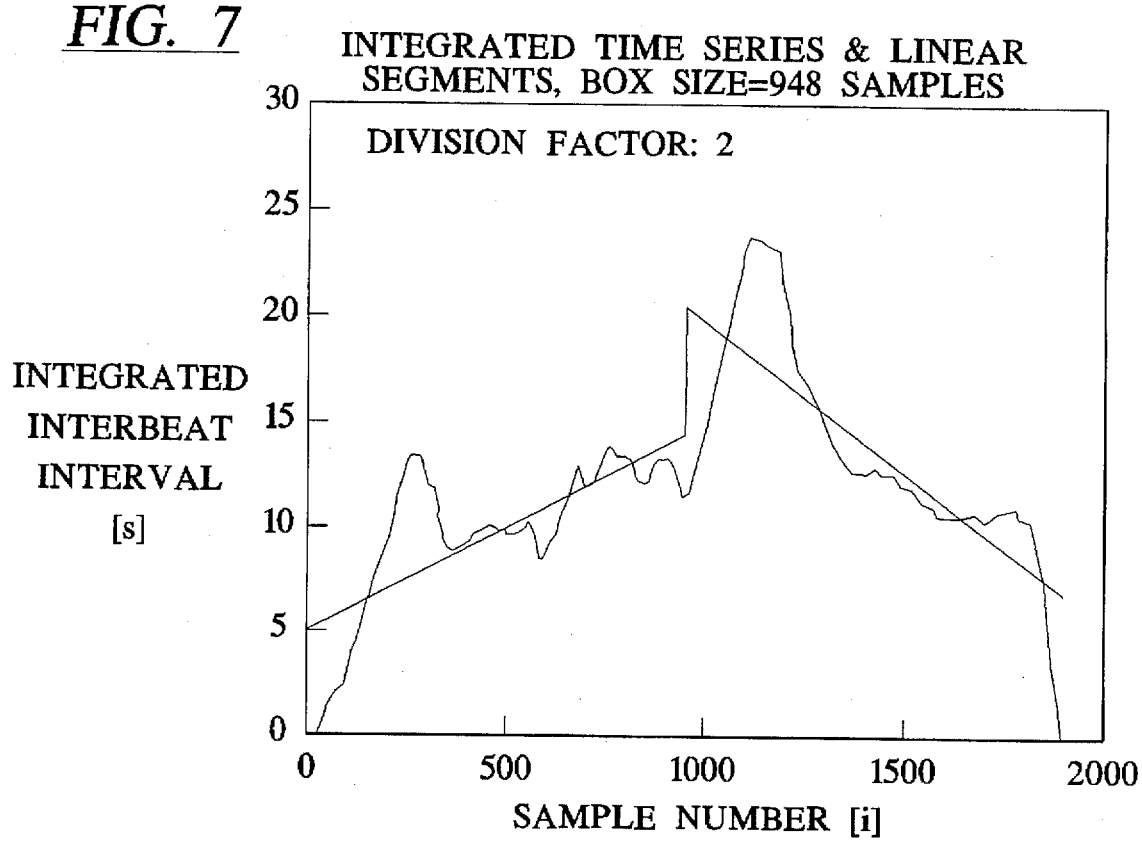
FIG. 7 shows a straight line fit with a division factor of 2 for the integrated interbeat interval curve of FIG. 5.

This procedure is then repeated for a number of increasingly shorter intervals (i.e., decreasing number of samples in the box size). FIG. 7 shows the straight line fit using a division factor of 2 in which case the value of F (now designated F2) is F2=2.721.

Figure 8:
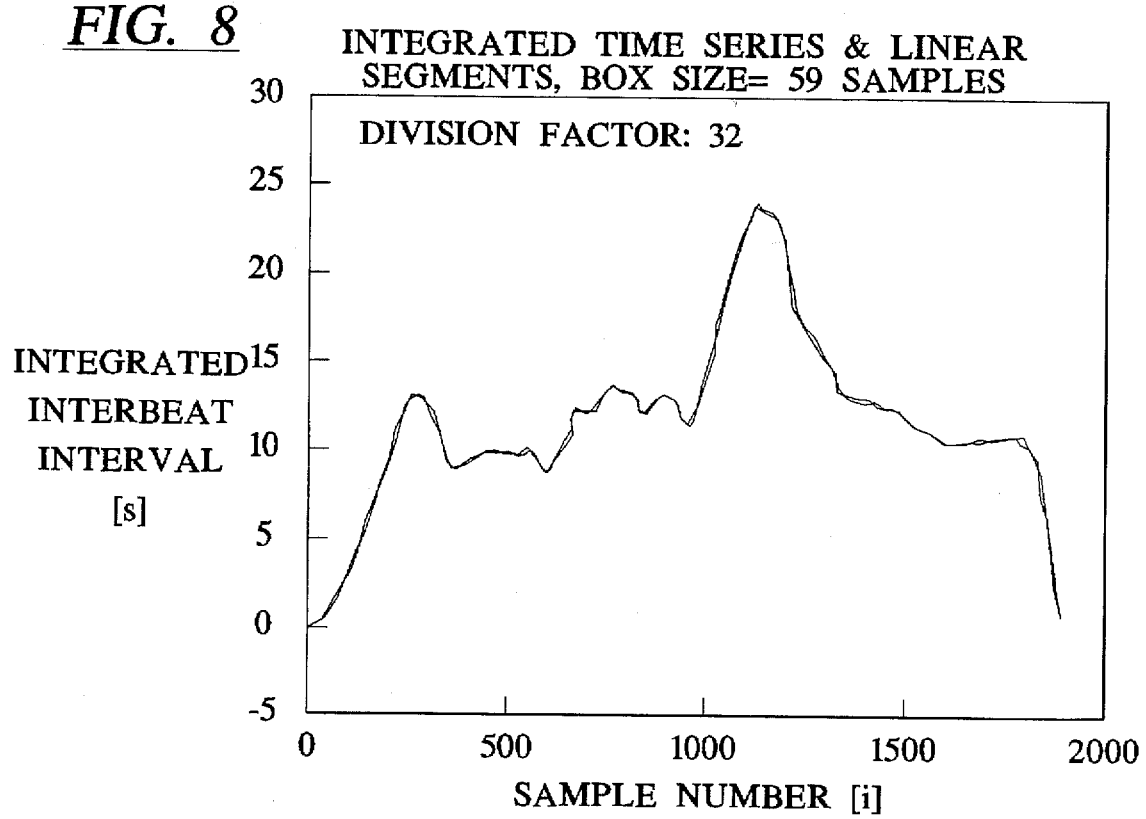
FIG. 8 shows a straight line fit with a division factor of 32 for the integrated interbeat interval curve of FIG. 5.

FIG. 8 shows the straight line fit with a division factor 32, which results in F32=0.1967.

For eight different division factors, the following table results:

| Division Factor | Box Size n (# of samples) | # of Boxes | Length of Analyzed Interval | F |
| --- | --- | --- | --- | --- |
| 1 | 1897 | 1 | 1897 | 4.593 |
| 2 | 948 | 2 | 1896 | 2.721 |
| 4 | 474 | 4 | 1896 | 2.527 |
| 8 | 237 | 8 | 1896 | 1.035 |
| 16 | 118 | 16 | 1888 | 0.4857 |
| 32 | 59 | 32 | 1888 | 0.1967 |
| 64 | 29 | 65 | 1885 | 0.09003 |
| 128 | 14 | 135 | 1890 | 0.0354 |

In order to make the number of samples in the box size divide evenly into the total number of samples, in some instances a small number of samples has been ignored.

It should again be emphasized that the above-calculations are all for the same signal, but over increasingly smaller subsets of that signal.

Figure 9:
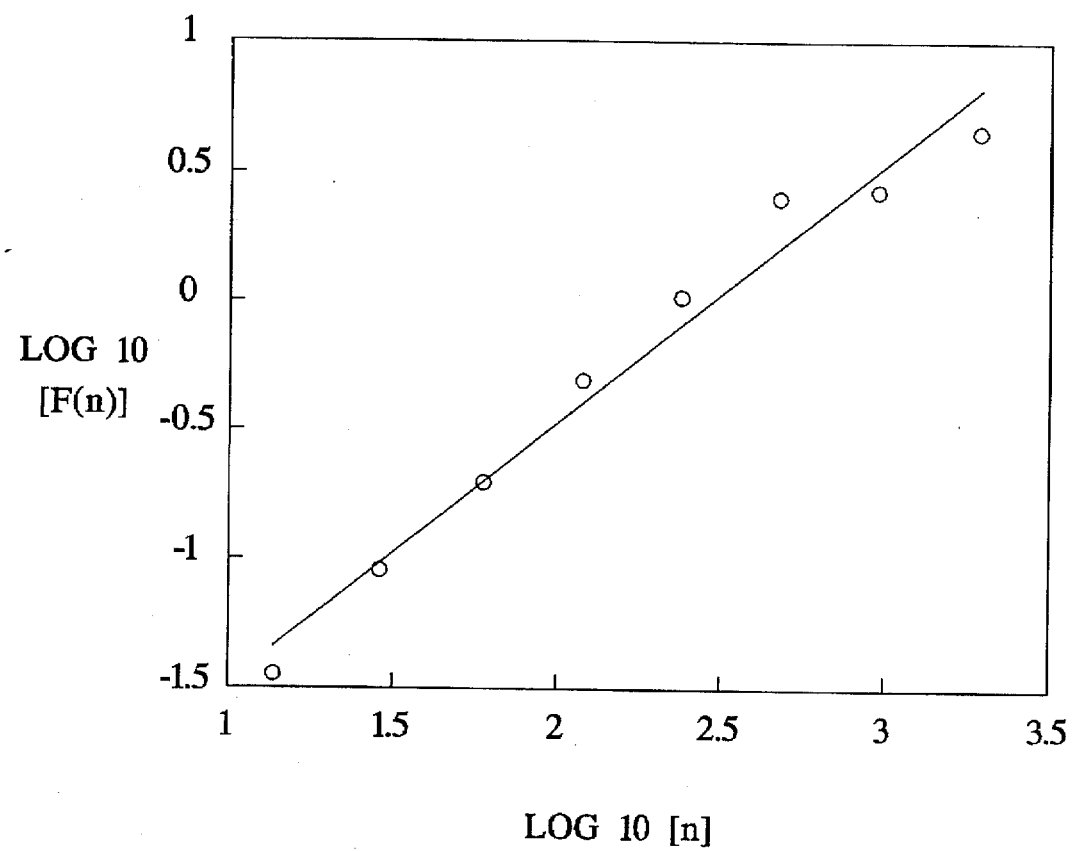
FIG. 9 shows how an index is obtained in an apparatus constructed in accordance with the invention using detrended fluctuation analysis from a straight line fit to a number of calculated points obtained using different division factors.

The last step is the index calculation, which is obtained by plotting the logarithm of the number of samples in a box n versus the logarithm of the variability F(n). The result of such a plot for base 10 logarithms (any logarithm base can be used) is shown in FIG. 9, wherein the circles indicate the plotted values. A best fit straight line is then calculated by any suitable method, such a straight line also being entered in FIG. 9. The slope of this straight line is the self-similarity parameter, designated "alpha" in FIG. 9. In the exemplary embodiment, the self-similarity parameter is 1.014, which is very close to 1.0, indicating that the subject has a healthy cardiac status. As noted earlier, if the straight line fit to the logarithmic plot of FIG. 9 had exhibited a steeper slope, the extent to which this steeper slope deviates from 1.0 would be indicative of the cardiac risk of the subject, with a slope of 1.3, for example, indicating the presence of ischemia.

Other signals representative of cardiac activity, or physiological activity related to cardiac activity, can be used instead of the interbeat interval. For example, maximal pressure dP/dt in the right ventricle on beat-to-beat basis could be measured, or the average of the peak-to-peak bipolar impedance over five beats could be obtained, or the average of any calculated parameter over a relatively short fixed interval can be used.

Figure 10:
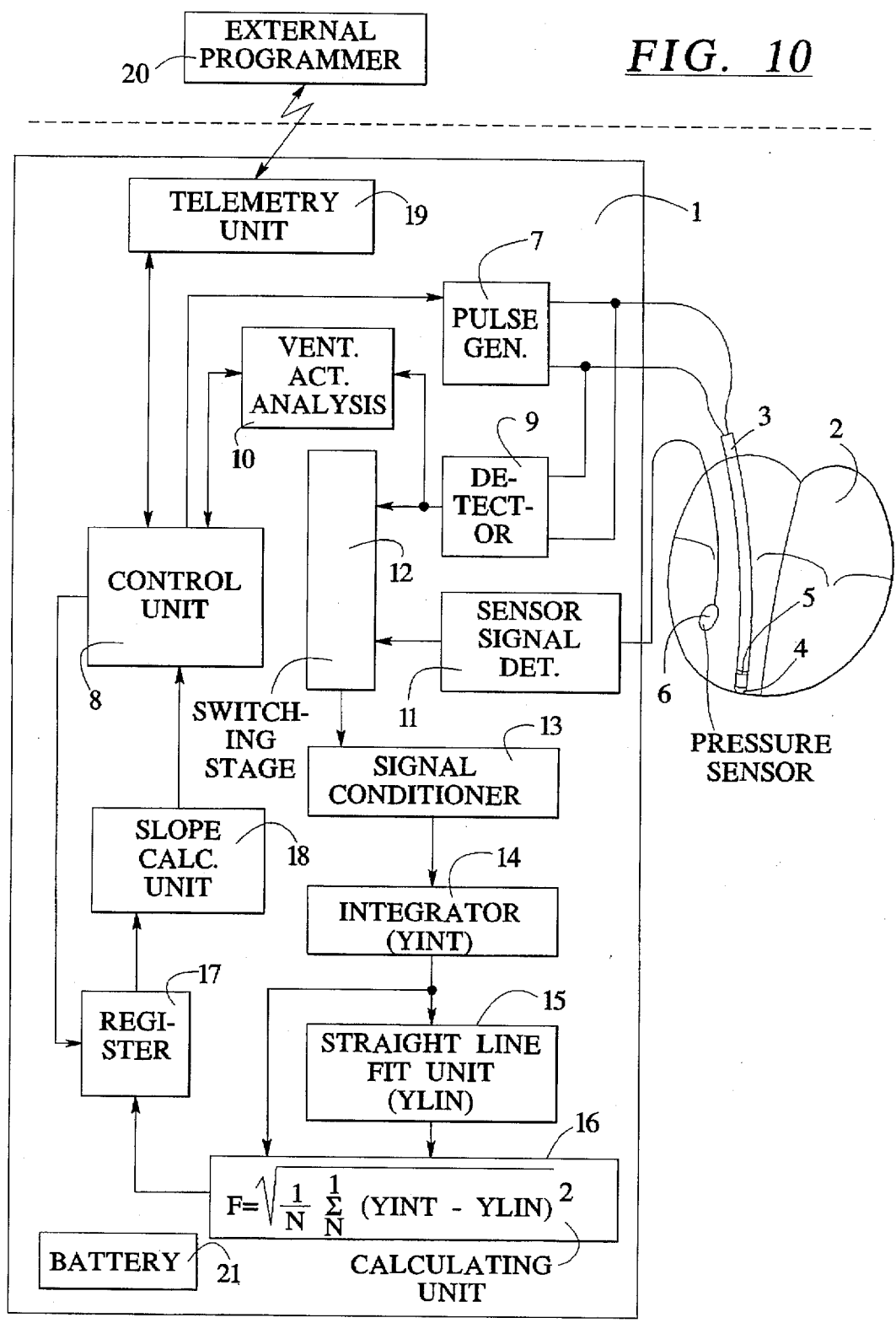
FIG. 10 is a schematic block diagram of a pacemaker employing detrended functional analysis constructed and operating in accordance with the principles of the present invention.

An example of an implantable pacemaker which affords the possibility of using either the interbeat interval, as obtained in a standard manner from the IECG, or ventricular pressure, is shown in FIG. 10. Although FIG. 10 shows an exemplary embodiment of a pacemaker, the invention is not limited to an implantable pacemaker, and encompasses any type of implantable medical apparatus wherein therapy is administered dependent, at least in part, on a measured physiological signal.

The pacemaker shown in FIG. 10 has a housing 1 of a size and shape adapted for implantation in a subject. Implantation is schematically indicated in FIG. 10 by the dashed line indicating the patient's skin surface.

The electrical components, described in detail below, contained in the housing 1 interact with the patient's heart 2 via an implanted lead 3. In the embodiment shown in FIG. 10, a bipolar lead 3, having a tip electrode 4 and a ring electrode 5, is shown implanted in the ventricle. The type of lead and the pacing site and the number of leads, however, are not important to the subject matter of the invention. The invention can be used with a unipolar lead placed in the atrium or in the ventricle, or can be used with dual chamber pacing.

FIG. 10 also shows, for exemplary purposes, a physiological sensor in the form of a pressure sensor 6, however, the invention is not limited to the use of a pressure sensor as the physiological sensor, and any suitable type of physiological sensor can be employed.

In a known manner, pacing pulses are generated in a pulse generator 7 and are supplied via the lead 3 to the tip electrode 4. The pulses are generated according to a therapy regimen controlled by a control unit 8 connected to the pulse generator 7. Following emission of a stimulation pulse via the tip electrode 4, ventricular activity is sensed between the tip electrode 4 and the ring electrode 5, the sensed activity (IECG) being acquired by a detector (sense amplifier) 9, also connected to the lead 3. The output of the detector 9 is supplied to a ventricular activity analysis unit 10 which conducts any suitable type of ventricular activity analysis in a known manner. The ventricular activity analysis unit 10 supplies an output signal to the control unit 8 which, dependent on that output signal, may determine that changes in the therapy are warranted.

The measurement signal obtained by the pressure sensor 6 is supplied to a sensor signal detector 11. The output of the sensor signal detector 11, together with the output of the detector 9, is supplied to a switching stage 12. The switching stage 12 is operated by the control unit 8 to forward a selected one of the output of the detector 9 or the output of the sensor signal detector 11 to a signal conditioner 13. The signal conditioner 13 includes standard components such as filters and amplifiers and A/D converters (if the subsequent analysis is to be undertaken digitally) for conditioning the signal, in a known manner, for further analysis. Such signal conditioning may also take place in an input stage of the ventricular activity analysis unit 10 or, in order to avoid redundancy, the output of the detector 9 can always be supplied to the signal conditioner 13 and the output of the signal conditioner 13 can be switched, under the control of the control unit 8, so as to be supplied either to the ventricular activity analysis unit 10 (without, in this case, a signal conditioning input stage) or to the integrator 14. Depending on the state of the switching stage 12, either the output of the detector 9 (ventricular activity) or the output of the sensor signal detector 11 (in this case, a measurement of ventricular pressure) is supplied to the input of the integrator 14 to begin the detrended fluctuation analysis. The control unit 8 may alternate which of the outputs of the detector 9 or the sensor signal detector 11 is used for this analysis so that an index for the ventricular activity as well as an index for the ventricular pressure signal (or whatever other physiological activity is sensed) are obtained.

The output signal from the signal conditioner 13 is integrated in the integrator 14 to obtain the aforementioned value YINT as the output of the integrator 14. In the above-described exemplary embodiment, the output of the integrator 14 would be the curve as shown in FIG. 5.

The output of the integrator 14 is supplied to a straight line fit unit 15, which calculates a best fit straight line for the curve represented by the output of the integrator 14, as shown for the exemplary embodiment in FIG. 6. The output of the straight line fit unit 15 is YLIN.

The output of the integrator 14 is directly supplied, together with the output of the straight line fit unit 15, to a calculating unit 16, wherein the aforementioned values F are calculated according to the above-described formula. The calculating unit 16 can itself include a suitable stored algorithm for repeating the calculation over successively shorter intervals, or it can do so under the control of the control unit 8. The successive calculation results obtained in the calculating unit 16 are supplied to a register 17. After the requisite number of values is obtained from the calculating unit 16 (eight such values in the above example), the stored values from the register 17, upon a signal from the control unit 8, are transferred to a slope calculation unit 18, wherein a best fit straight line is obtained, as shown for the above example in FIG. 9. The slope of this straight line is calculated and is supplied as the aforementioned self-similarity parameter alpha to the control unit 8.

The control unit 8 includes, or is connected to, a data memory wherein the index is stored. The aforementioned index calculation procedure can be undertaken as often as warranted, such as daily or weekly, so that a data base of indices is developed in the memory associated with the control unit 8. This data base can be read out by a physician via a telemetry unit 19, and the indices can be represented on the display of an external programmer 20, so that a physician can evaluate the indices individually as well as identifying a trend, if any, over time in changes in the indices. For example, if in order to treat a previously-diagnosed cardiac pathology the patient has been placed on a drug regimen, the effectiveness of the drug regimen can be ascertained by evaluating the changes, if any, in the self-similarity parameter over time. If the parameter is changing in a direction toward a value of 1.0, this is an indication that the drug regimen is having the desired effect. If no changes are perceived, or if the index continues to proceed increasingly away from a value of 1.0, a new regimen can be prescribed.

If an index is obtained for each of the output signals from the detector 9 and the sensor signal detector 11, these signals can be used as a check against each other. If the respective indices for both of the different types of analyzed activity are moving in the same direction and by substantially the same amount, this is a strong indication that the patient's cardiac status is either improving or worsening, dependent on the direction of the change.

All of the power-consuming components within the housing 1 are connected to a battery 21 by printed circuit conductor runs in a known manner. The respective electrical connections between the battery 21 and the power-consuming components are not shown in FIG. 10 since they are well understood by those of ordinary skill in the art.

In addition to making the self-similarity parameter alpha extracorporeally available via the telemetry unit 19 and the external programmer 20, this parameter can be used by the control unit 8 to adjust the pacing regimen emitted by the pulse generator 7. This can be accomplished in many ways. For example, in the analysis of the ventricular activity used by the ventricular activity analysis unit 10, comparison of the current ventricular activity, or a value derived therefrom, can be made with respect to one or more reference values, such as a threshold. The control unit 8 can continually adjust this reference value dependent on the value of the self-similarity parameter.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical apparatus comprising:

a housing having a size and shape adapted for implantation in a subject;

therapy means disposed in said housing for producing a medical therapy regimen;

means connected to said therapy means and adapted for interaction with the subject for delivering said medical therapy regimen in vivo to the subject;

sensor means adapted for interaction with the subject for obtaining an electrical signal representing physiological activity of the subject;

signal analysis means disposed in said housing and connected to said sensor means, for performing detrended fluctuation analysis of said electrical signal and thereby obtaining a self-similarity parameter for said electrical signal; and means for making said self-similarity parameter extracorporeally available.

2. A medical apparatus as claimed in claim 1 wherein said therapy means comprise means for emitting cardiac pacing pulses.

3. A medical apparatus as claimed in claim 1 wherein said sensor means comprise means for obtaining an electrical signal representing ventricular electrical activity.

4. A medical apparatus as claimed in claim 1 wherein said sensor means comprise means for obtaining an electrical signal representing ventricular blood pressure.

5. A medical apparatus as claimed in claim 1 further comprising means for sampling said electrical signal to obtain a total number of samples;

means for separately integrating said electrical signal over said total number of samples and over a plurality of subsets of said total number of samples, each subset containing a different number of samples, each integration producing an integration curve having an integral value YINT;

means, for each integration curve, fitting a best fit straight line thereto and for identifying a linear trend YLIN for that best fit straight line;

means, for each associated integral value YINT and linear trend YLIN, for calculating a value F according to the formula $$F = \sqrt{\frac{1}{N} * \sum_{1}^{N} (YINT - YLIN)^2}$$

wherein N is the number of samples for the integral curve which produced YINT and YLIN; and means for identifying a further best fit straight line for all values of F for said electrical signal, said further best fit straight line having a slope comprising said self-similarity parameter.

6. A medical apparatus comprising:

a housing having a size and shape adapted for implantation in a subject;

therapy means disposed in said housing for producing a medical therapy regimen;

means connected to said therapy means and adapted for interaction with the subject for delivering said medical therapy regimen in vivo to the subject;

sensor means adapted for interaction with the subject for obtaining an electrical signal representing physiological activity of the subject;

signal analysis means disposed in said housing and connected to said sensor means, for performing detrended fluctuation analysis of said electrical signal and thereby obtaining a self-similarity parameter for said electrical signal; and control means for controlling production of said medical therapy regimen by said therapy means dependent on said self-similarity parameter.

7. A medical apparatus as claimed in claim 6 wherein said control means comprises means for comparing said electrical signal to a reference value and means for adjusting said reference value dependent on said self-similarity parameter.

8. A medical apparatus as claimed in claim 6 wherein said control means comprises means for comparing a value derived from said electrical signal to a reference value and means for adjusting said reference value dependent on said self-similarity parameter.

9. A medical apparatus as claimed in claim 6 wherein said therapy means comprise means for emitting cardiac pacing pulses.

10. A medical apparatus as claimed in claim 6 wherein said sensor means comprise means for obtaining an electrical signal representing ventricular electrical activity.

11. A medical apparatus as claimed in claim 6 wherein said sensor means comprise means for obtaining an electrical signal representing ventricular blood pressure.

12. A medical apparatus as claimed in claim 6 further comprising means for sampling said electrical signal to obtain a total number of samples;

means for separately integrating said electrical signal over said total number of samples and over a plurality of subsets of said total number of samples, each subset containing a different number of samples, each integration producing an integration curve having an integral value YINT;

means, for each integration curve, fitting a best fit straight line thereto and for identifying a linear trend YLIN for that best fit straight line;

means, for each associated integral value YINT and linear trend YLIN, for calculating a value F according to the formula $$F = \sqrt{\frac{1}{N} * \sum_{1}^{N}(YINT - YLIN)^2}$$

wherein N is the number of samples for the integral curve which produced YINT and YLIN; and means for identifying a further best fit straight line for all values of F for said electrical signal, said further best fit straight line having a slope comprising said self-similarity parameter.

13. A cardiac pacemaker comprising:

a housing having a size and shape adapted for implantation in a subject;

pulse generator means disposed in said housing for emitting a pacing regimen comprising a plurality of pacing pulses;

an electrode lead connected to said pulse generator means and terminating in at least one electrode for interaction with said subject for delivering said pacing pulses in vivo to said subject;

sensor means adapted for interaction with the subject for obtaining at least one electrical signal representing physiological activity of the subject;

signal analysis means disposed in said housing and connected to said sensor means for performing detrended fluctuation analysis of said electrical signal and thereby obtaining a self-similarity parameter for said electrical signals; and telemetry means in said housing for making said self-similarity parameter extracorporeally available.

14. A cardiac pacemaker as claimed in claim 13 wherein said sensor means comprise a ring electrode on said electrode lead for obtaining an electrical signal representing ventricular electrical activity.

15. A cardiac pacemaker as claimed in claim 13 wherein said sensor means comprise a pressure sensor for obtaining an electrical signal representing ventricular blood pressure.

16. A cardiac pacemaker as claimed in claim 13 wherein said sensor means comprise means for obtaining a first electrical signal representing a first physiological activity of the subject and means for obtaining a second electrical signal representing a second physiological activity of the subject, and switching means for supplying a selected one of said first and second electrical signals to said signal analysis means.

17. A cardiac pacemaker as claimed in claim 13 wherein said sensor means comprise means for obtaining a first electrical signal representing a first physiological activity of the subject and means for obtaining a second electrical signal representing a second physiological activity of the subject, and switching means for alternatively supplying said first and second electrical signals to said signal analysis means.

18. A cardiac pacemaker as claimed in claim 13 further comprising:

control means for adjusting said pacing regimen generated by said pulse generator means dependent on said self-similarity parameter.

19. A cadiac pacemaker as claimed in claim 18 wherein said control means comprises means for comparing said electrical signal to a reference value and means for adjusting said reference value dependent on said self-similarity parameter.

20. A caridac pacemaker as claimed in claim 18 wherein said control means comprises means for comparing a value derived from said electrical signal to a reference value and means for adjusting said reference value dependent on said self-similarity parameter.

21. A cardiac pacemaker as claimed in claim 13 wherein said therapy means comprise means for emitting cardiac pacing pulses.

22. A cardiac pacemaker as claimed in claim 13 wherein said sensor means comprises means for obtaining an electrical signal representing ventricular electrical activity.

23. A cardiac pacemaker as claimed in claim 13 wherein said sensor means comprise means for obtaining an electrical signal representing ventricular blood pressure.

24. A cardiac pacemaker as claimed in claim 13 further comprising means for sampling said electrical signal to obtain a total number of samples;

means for separately integrating said electrical signal over said total number of samples and over a plurality of subsets of said total number of samples, each subset containing a different number of samples, each integration producing an integration curve having an integral value YINT;

means, for each integration curve, fitting a best fit straight line thereto and for identifying a linear trend YLIN for that best fit straight line;

means, for each associated integral value YINT and linear trend YLIN, for calculating a value F according to the formula $$F = \sqrt{\frac{1}{N} * \sum_{1}^{N}(YINT - YLIN)^2}$$

wherein N is the number of samples for the integral curve which produced YINT and YLIN; and means for identifying a further best fit straight line for all values of F for said electrical signal, said further best fit straight line having a slope comprising said self-similarity parameter.

* * * * *